(12) United States Patent
Robichaud (10) Patent No.: US 10,456,273 B2
(45) Date of Patent: Oct. 29, 2019

(54) SURGICAL CUT VALIDATION TOOL AND METHOD

(71) Applicant: LABORATOIRES BODYCAD INC., Quebec (CA)

(72) Inventor: Jean Robichaud, Quebec (CA)

(73) Assignee: LABORATOIRES BODYCAD INC., Québec (CA)

( * ) Notice: Subject to any disclaimer, the term of this patent is extended or adjusted under 35 U.S.C. 154(b) by 413 days.

(21) Appl. No.: 14/896,889

(22) PCT Filed: Jun. 11, 2014

(86) PCT No.: PCT/CA2014/050541
§ 371 (c)(1),
(2) Date: Dec. 8, 2015

(87) PCT Pub. No.: WO2014/197987
PCT Pub. Date: Dec. 18, 2014

(65) Prior Publication Data
US 2016/0113784 A1    Apr. 28, 2016

Related U.S. Application Data

(60) Provisional application No. 61/834,534, filed on Jun. 13, 2013.

(51) Int. Cl.
*A61F 2/46* (2006.01)
*A61B 34/10* (2016.01)
(Continued)

(52) U.S. Cl.
CPC ............ *A61F 2/4657* (2013.01); *A61B 34/10* (2016.02); *G06F 17/50* (2013.01);
(Continued)

(58) Field of Classification Search
CPC ............ A61B 2017/681; A61B 17/155; A61B 17/157; A61F 2/46
See application file for complete search history.

(56) References Cited

U.S. PATENT DOCUMENTS 5,486,180 A * 1/1996 Dietz ................. A61B 17/1764
606/86 R
5,916,220 A * 6/1999 Masini ................. A61B 17/155
606/87
(Continued)

FOREIGN PATENT DOCUMENTS

| CA | 2209498 A1 | 8/1996 |
| CA | 2764002 A1 | 12/2010 |
| WO | WO-2009109669 A1 | 9/2009 |

OTHER PUBLICATIONS

Written Opinion of the International Searching Authority and International Search Report for International Application No. PCT/CA2014/050541, dated Aug. 21, 2014.

*Primary Examiner* — David W Bates
(74) *Attorney, Agent, or Firm* — Marshall, Gerstein & Borun LLP (57) ABSTRACT

A method of manufacturing a surgical cut validation tool is discussed. A digital bone representation representing a bone is received including a virtual bone outer surface. At least one cutting plane is positioned intersecting the virtual bone outer surface. A digital tool representation representing the tool is created, including a virtual planar surface corresponding to each cutting plane and a virtual tool outer surface with a virtual border surface portion. The virtual border surface portion extends from a junction between the virtual tool outer surface and each virtual planar surface. At least part of the virtual border surface portion is defined from a corresponding portion of the virtual bone outer surface such as to represent a corresponding portion of the bone outer surface.

(Continued)

The tool body is manufactured using the digital tool representation. A tool and a method of validating a cut in a bone are also provided.

25 Claims, 9 Drawing Sheets

(51) Int. Cl.
  *A61F 2/30*     (2006.01)
  *A61F 2/38*     (2006.01)
  *G06F 17/50*    (2006.01)
  *A61B 90/00*    (2016.01)

(52) U.S. Cl.
  CPC ... *A61B 2034/108* (2016.02); *A61B 2090/061* (2016.02); *A61F 2/30942* (2013.01); *A61F 2/389* (2013.01); *A61F 2002/4658* (2013.01)

(56) References Cited

U.S. PATENT DOCUMENTS

| | | | |
|---|---|---|---|
| 8,414,653 B2 | 4/2013 | Burstein et al. | |
| 8,728,086 B2* | 5/2014 | Smith | A61B 17/155 606/88 |
| 9,414,846 B2* | 8/2016 | Gillman | A61B 17/154 |
| 9,498,233 B2* | 11/2016 | Eash | A61B 17/1746 |
| 2004/0153086 A1* | 8/2004 | Sanford | A61B 17/155 606/88 |
| 2007/0226986 A1* | 10/2007 | Park | A61B 17/155 29/592 |
| 2008/0119938 A1* | 5/2008 | Oh | A61B 17/155 623/20.14 |
| 2009/0087276 A1* | 4/2009 | Rose | A61B 17/155 409/79 |
| 2009/0222014 A1* | 9/2009 | Bojarski | A61B 17/155 606/88 |
| 2011/0106093 A1* | 5/2011 | Romano | A61B 17/155 606/88 |
| 2011/0144760 A1* | 6/2011 | Wong | A61F 2/30942 623/20.14 |
| 2011/0184526 A1* | 7/2011 | White | A61B 17/154 623/20.32 |
| 2012/0041445 A1* | 2/2012 | Roose | A61B 17/1746 606/96 |
| 2012/0116562 A1* | 5/2012 | Agnihotri | A61B 17/155 700/98 |
| 2012/0123423 A1* | 5/2012 | Fryman | A61B 17/15 606/89 |
| 2012/0143198 A1* | 6/2012 | Boyer | A61B 17/151 606/87 |
| 2012/0209394 A1 | 8/2012 | Bojarski et al. | |
| 2012/0296339 A1* | 11/2012 | Iannotti | A61B 17/15 606/87 |
| 2014/0066937 A1* | 3/2014 | Wiebe, III | A61B 17/1764 606/88 |
| 2014/0074100 A1* | 3/2014 | Murray | A61B 17/155 606/88 |
| 2014/0114319 A1* | 4/2014 | Wilkinson | A61B 17/1764 606/88 |
| 2014/0336660 A1* | 11/2014 | Gibson | A61F 2/4609 606/91 |
| 2018/0116804 A1* | 5/2018 | Hafez | A61B 17/155 |
| 2018/0185097 A1* | 7/2018 | Langhorn | A61B 34/10 |

\* cited by examiner

SURGICAL CUT VALIDATION TOOL AND METHOD

CROSS-REFERENCE TO RELATED APPLICATIONS

This application claims the benefit of the filing date, under 35 USC § 119(e), of U.S. provisional patent application 61/834,534, filed on Jun. 13, 2013, the entirety of which is hereby incorporated by reference. This application is a US national phase entry of PCT patent application serial number PCT/CA2014/050541, filed on Jun. 11, 2014, (now pending) designating the United States of America.

TECHNICAL FIELD

The application relates generally to orthopedic instruments and, more particularly, to a validation tool for use during orthopedic surgery.

BACKGROUND OF THE ART

In joint replacement surgeries, sections of bones are removed and replaced by corresponding prosthesis. Typically, the surgeon selects a prosthesis size proportional to the bone size of the patient, and cuts the bone in order to match the size of the prosthesis, using cutting guides corresponding to the particular prosthesis being put in place. Validation blocks, which are typically prismatic, are inserted in the bone cut to validate that the bone has been cut to the proper size; if the block cannot be inserted, additional bone is cut until it can. Cement may also be used to compensate for poor cuts or uneven bones.

SUMMARY

In one aspect, there is provided a method of manufacturing a surgical cut validation tool, the method comprising: receiving a digital bone representation representing a bone, the digital bone representation including a virtual bone outer surface representing an outer surface of the bone at least for and around a section to be cut; positioning at least one cutting plane intersecting the virtual bone outer surface in the digital bone representation, each cutting plane representing a cut surface of the section to be cut; creating a digital tool representation representing the cut validation tool, including creating a virtual planar surface along each cutting plane, and creating a virtual tool outer surface including a virtual border surface portion, the virtual border surface portion extending from a junction between the virtual tool outer surface and each virtual planar surface, at least part of the virtual border surface portion being defined from a corresponding portion of the virtual bone outer surface such as to represent a corresponding portion of the outer surface of the bone; and manufacturing a body of the cut validation tool using the digital tool representation, including manufacturing a planar surface corresponding to each virtual planar surface and an outer surface corresponding to the virtual tool outer surface.

In another aspect, there is provided a surgical cut validation tool for validating a cut in a bone, the tool comprising: a body having at least one planar surface, and an outer surface extending from the at least one planar surface, the outer surface including a border surface portion extending from a junction between the outer surface and each planar surface; wherein each planar surface corresponds to a predetermined cut surface of a nominal section to be removed from the bone; and at least part of the border surface portion has a shape corresponding to that of part of an outer surface of the nominal section, the at least part of the border surface portion having a same relative position with respect to each planar surface than the part of the outer surface of the nominal section with respect to the each predetermined cut surface.

In a further aspect, there is provided a method of validating a cut in a bone, the method comprising: a) inserting a body of a tool into a cut section of the bone defined by at least one cut surface, the body having a planar surface in contact with each of the at least one cut surface; b) moving the body in the cut section until an outer surface of the body and an outer surface of the bone adjacent each of the at least one cut surface are at a closest alignment with one another; c) determining if a reference portion of the outer surface of the tool adjacent the cut surface protrudes beyond a corresponding portion of the outer surface of the bone; and d) if the reference portion of the outer surface of the tool protrudes beyond the corresponding portion of the outer surface of the bone, removing the body from the cut section, increasing a size of the cut section, and repeating steps a) to c).

DESCRIPTION OF THE DRAWINGS

Reference is now made to the accompanying figures in which.

DETAILED DESCRIPTION

In the present specification, including claims, "planar surface" includes smooth surfaces (e.g. extending completely within a plane) and textured surfaces (e.g. the contact points thereof being located within a plane) such as for example a surface including a series of spaced apart ridges or protrusions extending therefrom.

Figure 1:
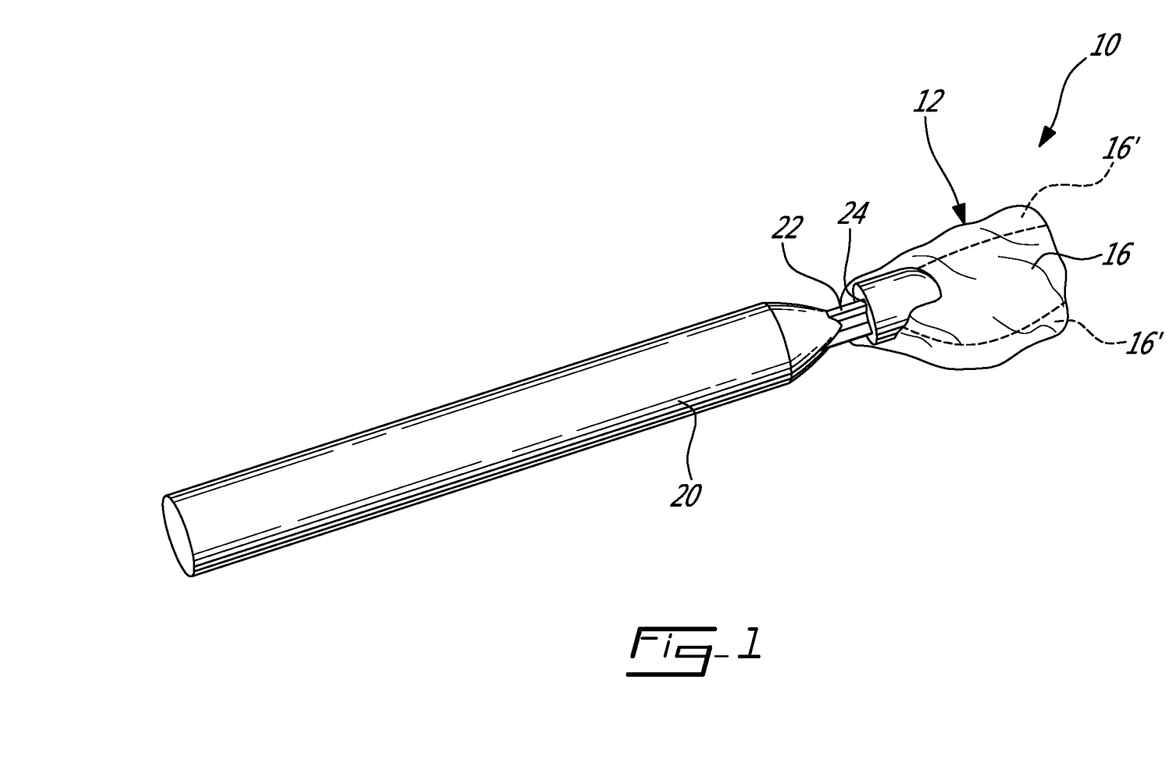
FIG. 1 is a tridimensional schematic view of a surgical cut validation tool in accordance with a particular embodiment.
Figure 2:
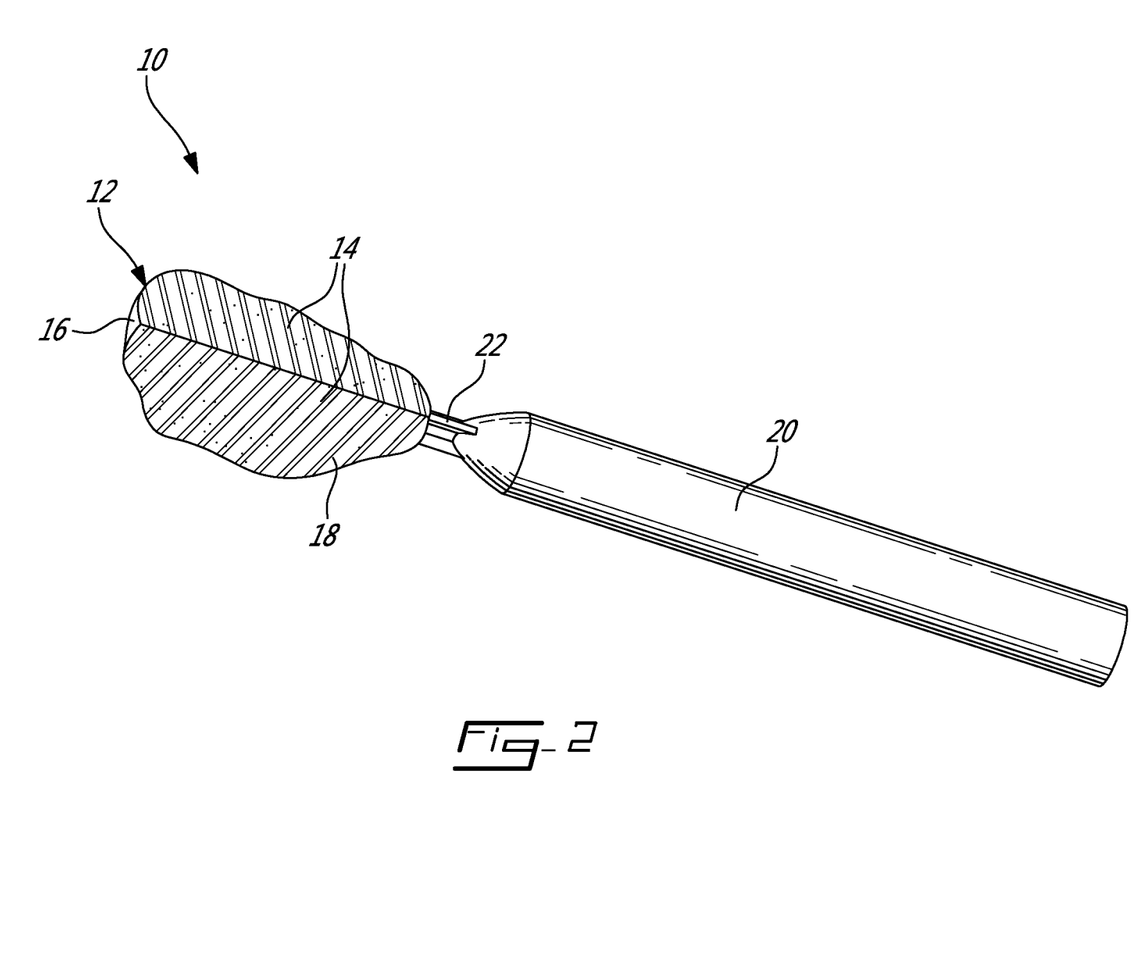
FIG. 2 is another tridimensional schematic view of the tool of FIG. 1.

Referring to FIGS. 1-2, a surgical cut validation tool 10 is shown. The tool 10 includes a body having at least one planar surface; in the embodiment shown, the body 12 includes two intersecting planar surfaces 14 (FIG. 2). The body 12 also includes an outer surface 16 extending from the planar surfaces 14. The tool 10 is designed to validate a cut in a bone and/or the fit between a custom or patient-specific prosthesis adapted to fit the patient's unique anatomy and designed to replace the cut section of the bone and an adjacent bone or prosthesis, as will be further detailed below.

As such, each planar surface 14 corresponds to a predetermined cut surface of a particular nominal removed bone section (i.e. the bone section which is required to be removed for replacement with a given prosthesis), and thus shaped to be received against a respective cut surface of the remaining bone. The outer surface 16 includes a border surface portion 16' (FIG. 1) extending from the junction of the outer surface 16 and each planar surface 14. At least part of this border portion 16' has a shape corresponding to that of a corresponding portion of the outer surface of the nominal removed bone section, i.e. to the portion of the nominal removed bone section's outer surface having the same relative position with respect to each predetermined cut surface than the relative position of this part of the border surface portion with respect to each planar surface. In a particular embodiment, this part of the border portion 16' is defined along an entirety of the junction with one of the planar surfaces 14. In another particular embodiment, the entirety of the border portion 16', i.e. the section of the outer surface 16 extending adjacent both planar surfaces 14, has a shape corresponding to that of the outer surface of the nominal removed bone section adjacent the cut surfaces.

In a particular embodiment, which may be used to validate the cut in the bone, the outer surface 16 completely corresponds to the outer surface of the removed bone section. In another particular embodiment, which may be used to validate the cut in the bone and the fit between the corresponding prosthesis and an adjacent prosthesis or bone, the remainder of the outer surface 16 (i.e., the outer surface 16 with the exception of the part of the border portion 16' corresponding to the outer surface of the nominal removed bone section) corresponds to the outer surface of the prosthesis. In a further embodiment, the remainder of the outer surface 16 has a generic shape, for example ovoid, planar, or defined as two or more intersecting planar surface sections. The shape of the outer surface 16 is patient-specific at least along the part of the border portion 16' corresponding to the outer surface of the nominal removed bone section, as will be further detailed below.

In a particular embodiment and as shown in FIG. 2, each planar surface 14 has a textured surface pattern, for example formed by a series of spaced apart ridges 18 extending therefrom. The textured surface pattern is configured such that the planar surface 14 can be used as a filing tool against the remaining bone, and the material of the body 12 is selected to have sufficient resistance to be usable to file a bone. Alternately, the textured surface pattern may be provided on only one of the planar surfaces 14.

In the embodiment shown, the tool 10 further includes a handle 20 extending from the body 12. In a particular embodiment, the handle 20 is detachably connected to the body 12. This may allow for identical handles to be manufactured in series to be used with different bodies, thus potentially minimizing manufacturing costs and/or time. In a particular embodiment, the handle 20 includes a tenon 22 which is snuggly received in a complementary mortise 24 defined in the body 12 and retained therein through friction.

In the embodiment shown, the tenon 22 and mortise 24 have a cross-shaped cross-section, but other cross-sectional shapes may also be used. Other types of attachment are also possible. Alternately, the handle 20 and body 12 may be monolithic, i.e. manufactured together as a single piece.

The handle 20 may be made of the same material as that of the body 12 or alternately be made of a different material.

Figure 3:
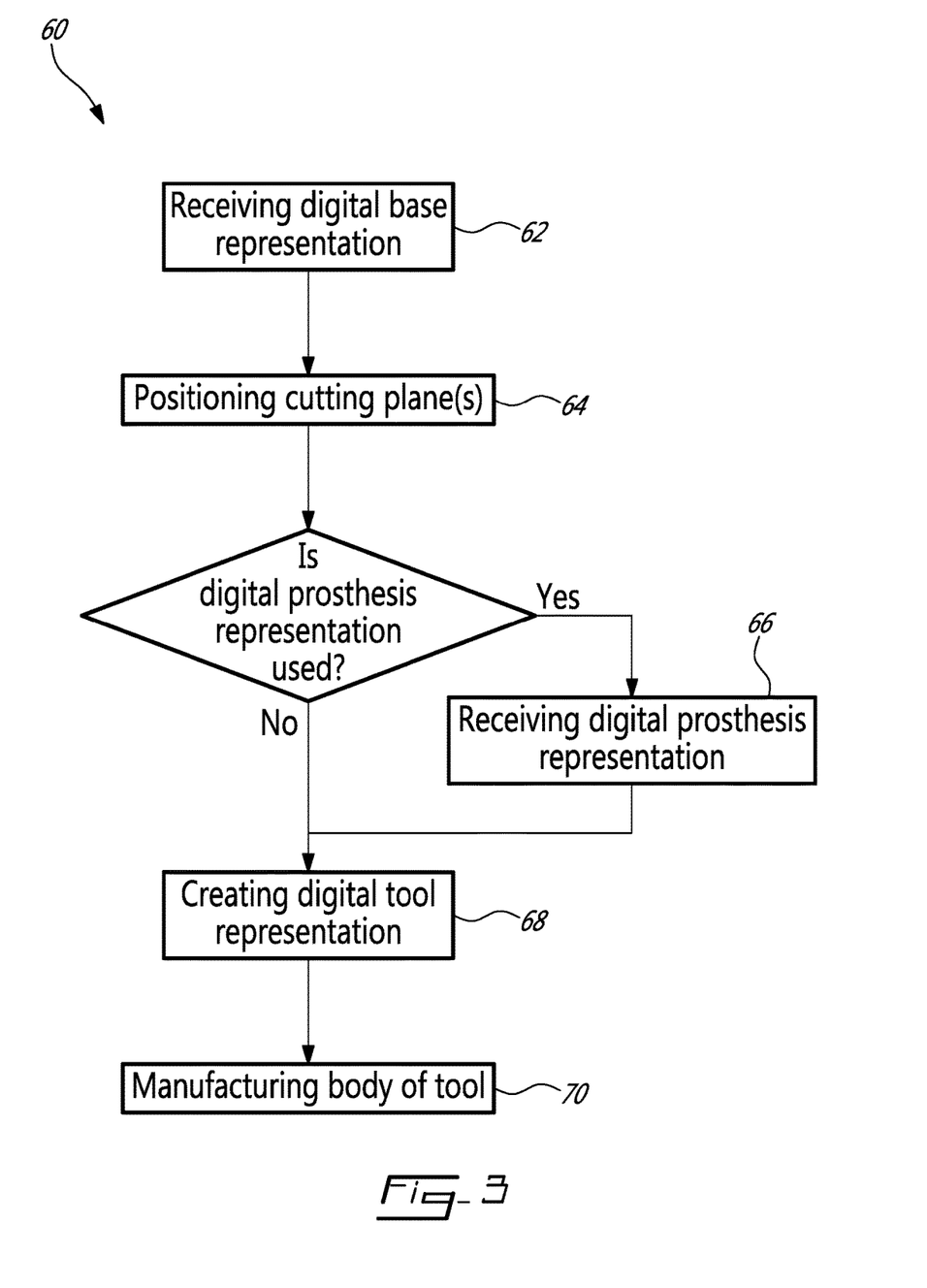
FIG. 3 is a flowchart of a method of manufacturing a body of a tool such as shown in FIG. 1, in accordance with a particular embodiment.
Figure 4:
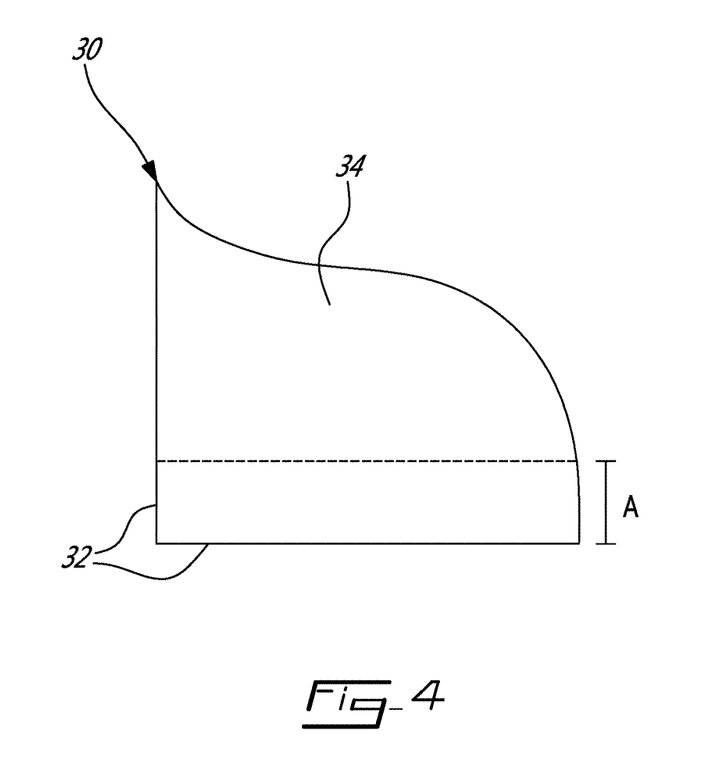
FIG. 4 is a schematic side view of a digital bone representation which may be used in the method of FIG. 3, in accordance with a particular embodiment.

In a particular embodiment, the body 12 is manufactured from a digital bone representation 30, an exemplary schematic illustration (e.g., screen shot of a CAD model) of which being illustrated in FIG. 4. In a particular embodiment, the body 12 is manufactured following the method 60 illustrated in FIG. 3. First, the digital bone representation 30 representing the bone to be cut for replacement by a prosthesis is received in a suitable processing system, as shown in step 62. The three-dimensional shape of the digital bone representation 30 is patient-specific and is created from the actual configuration of the bone of the patient. In a particular embodiment, the bone is a tibia and the prosthesis forms part of a knee joint. However, it should be understood that the method 60 may apply to other articular joints, such as an elbow, shoulder, wrist, or hip and to other types of bone-replacement prosthesis.

The digital bone representation 30 may be created from images of the bone and surrounding region obtained from scans generated using Magnetic Resonance Imaging (MRI), Computed Tomography (CT), ultrasound, x-ray technology, optical coherence tomography, or the like. Such images may be provided by a user, such as a medical technician, a surgeon, or a treating physician, via a suitable communication means to a computer system adapted to process the method 60. For this purpose, the user may electronically provide the scans of the patient's anatomy to the computer system via electronic mail, a Picture Archiving and Communication System (PACS) server, a website, or the like. The captured images may further be provided in various known formats, such as Digital Imaging and Communications in Medicine (DICOM), for handling, storing, printing, and transmitting information via PACS. Other exemplary formats are GE SIGNA Horizon LX, Siemens Magnatom Vision, SMIS MRD/SUR, and GE MR SIGNA 3/5 formats.

The images of the patient's bone and surrounding region may be processed and segmented. As images may be acquired along one or more planes throughout the body part, such as sagittal, coronal, and transverse, as well as multiple orientations, the data may be combined or merged during processing. The digital bone representation 30 may then be created from the segmented images.

Referring to FIG. 4, the digital bone representation 30 is three dimensional and includes a virtual bone outer surface 34 which represents the outer surface of the bone at least for and around the region to be cut.

Referring back to FIG. 3, at step 64, at least one virtual cutting plane 32 is defined and positioned in the digital bone representation 30, with each virtual cutting plane 32 representing a cut surface of the bone. Each virtual cutting plane 32 thus intersects the virtual bone outer surface 34. The position of the cutting plane(s) 32 is thus determined according to the physionomy of the particular bone, the type of prosthesis to be used, and/or any other appropriate parameter. In a particular embodiment where the section of the bone to be cut is a condyle, two intersecting cutting planes 32 are positioned.

Figure 6A:
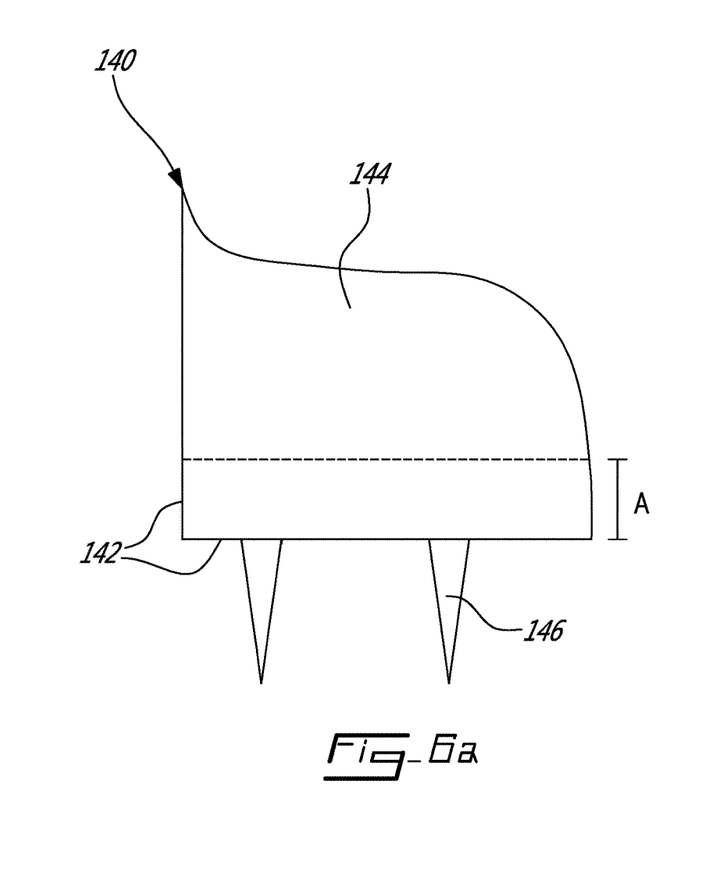
FIGS. 6a-6b are schematic side views of a digital prosthesis representation and of a digital tool representation, respectively, which may be used in the method of FIG. 3, in accordance with another particular embodiment.
Figure 6B:
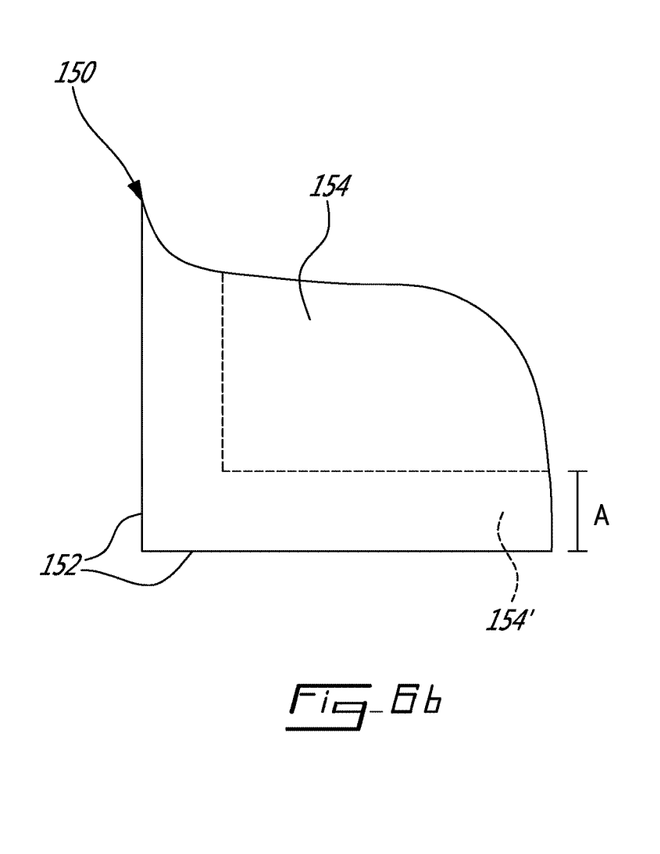
Figure 7A:
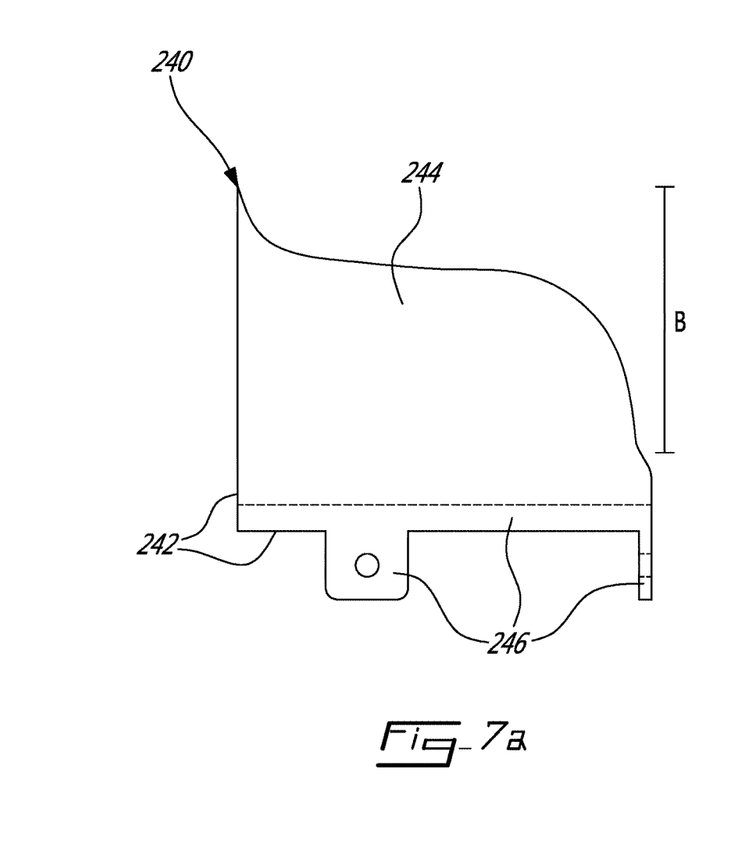
FIGS. 7a-7b are schematic side views of a digital prosthesis representation and of a digital tool representation, respectively, which may be used in the method of FIG. 3, in accordance with yet another particular embodiment.

In a particular embodiment, a digital prosthesis representation 140, 240 is used; exemplary schematic illustrations (e.g., screen shot of a CAD model) of which are shown in FIGS. 6a and 7a. Referring back to FIG. 3, and with reference to step 66, the digital prosthesis representation 140, 240 is received. The digital prosthesis representation 140, 240 is created from the digital bone representation 30, and represents a custom, patient-specific prosthesis designed for replacing the cut section of the bone. As shown in FIGS. 6a and 7a, the digital prosthesis representation 140, 240 includes a virtual contact surface 142, 242 corresponding to each virtual cutting plane 32 and representing a contact surface of the prosthesis with the remaining bone, and a virtual prosthesis outer surface 144, 244 extending from each virtual cutting plane, representing an outer surface of the prosthesis.

In another embodiment, the digital prosthesis representation 140, 240 is not used in the creation of the digital tool representation, and step 66 is omitted.

At step 68, the digital tool representation is then created, representing the body 12 of the tool 10. Exemplary schematic illustrations (e.g., screen shot of a CAD model) for the digital tool representation 50, 150, 250, 350 are shown in FIGS. 5, 6b, 7b and 8. The digital tool representation 50, 150, 250, 350 includes a virtual planar surface 52, 152, 252, 352 corresponding to each virtual cutting plane 32, each representing a contact surface of the body 12 with the remaining bone. The digital tool representation 50, 150, 250, 350 also includes a virtual tool outer surface 54, 154, 254, 354, extending from each virtual planar surface 52, 152, 252, 352, and representing the outer surface of the body 12. The virtual tool outer surface 54, 154, 254, 354 includes a virtual border surface portion 54', 154', 254', 354' extending from the junction between the virtual tool outer surface 54, 154, 254, 354 and each virtual planar surface 52, 152, 252, 352. At least part of the virtual border surface portion 54', 154', 254', 354' is defined from a corresponding portion of the virtual bone outer surface 34, such as to define the corresponding part of the border portion 16' of the tool 10 which is configured to correspond to the outer surface of the nominal removed bone section. Accordingly, in a particular embodiment, the part of the virtual border surface portion 54', 154', 254', 354' defined from a corresponding portion of the virtual bone outer surface 34 extends along an entirety of the junction with one of the virtual tool outer surface 54, 154, 254, 354. In another particular embodiment, the entirety of the virtual border surface portion 54', 154', 254', 354", i.e. the section of the virtual tool outer surface 54, 154, 254, 354 extending adjacent both virtual planar surface 52, 152, 252, 352, corresponds to the virtual bone outer surface 34.

Figure 5:
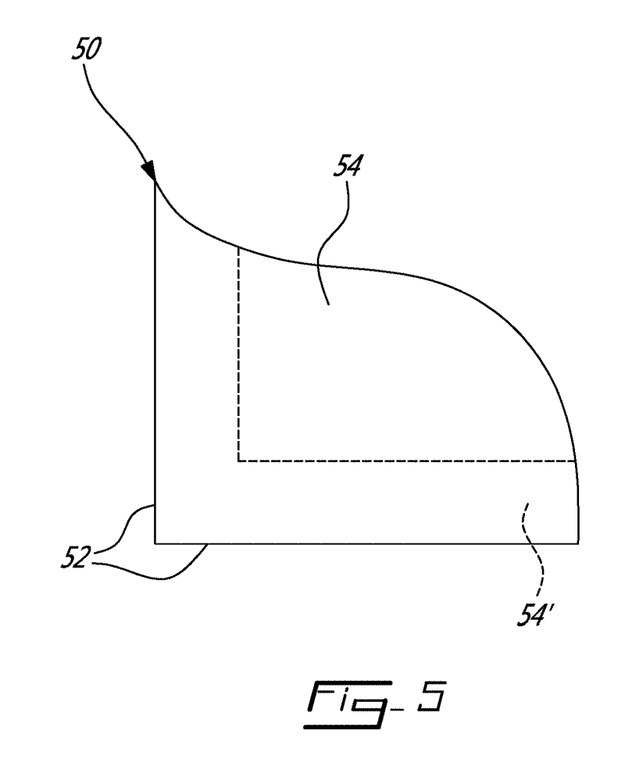
FIG. 5 is a schematic side view of a digital tool representation which may be used in the method of FIG. 3, in accordance with a particular embodiment.

In a particular embodiment where the digital prosthesis representation is not used and step 66 is omitted, the virtual tool outer surface completely corresponds to the virtual bone outer surface 34, such that the outer surface 16 of the body 12 of the tool 10 may represent a copy of the outer surface of the nominal removed bone section. An example of such a case is illustrated in FIG. 5. In this embodiment, the virtual tool outer surface 54, including the virtual border surface portion 54', is defined to completely correspond to the virtual bone outer surface 34 of the digital bone representation 30 (FIG. 4). For instance, the virtual tool outer surface 54 may be defined by making a copy of the virtual bone outer surface 34. In a particular embodiment, the virtual tool outer surface 54 and the virtual bone outer surface 34 are identical.

Figure 8:
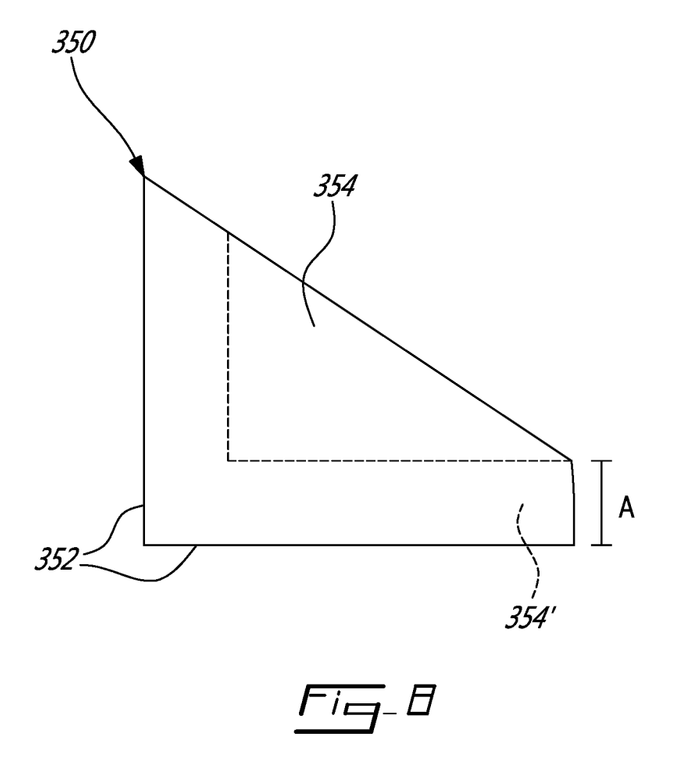
FIG. 8 is a schematic side view of a digital tool representation which may be used in the method of FIG. 3, in accordance with a further particular embodiment.
Figure 9:
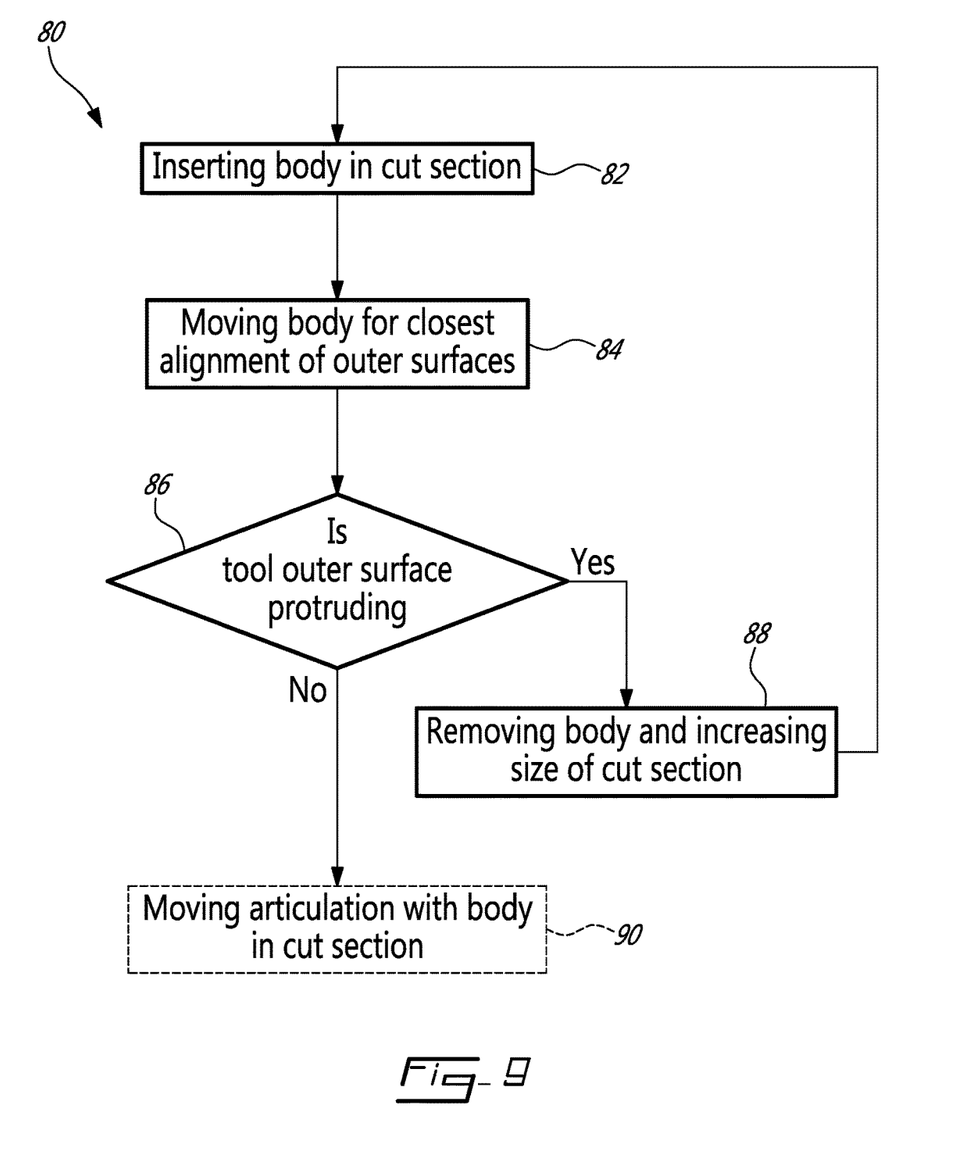
FIG. 9 is a flowchart of a method of validating a cut section of a bone with a body of a tool such as shown in FIG. 1, in accordance with a particular embodiment.
Figure 10:
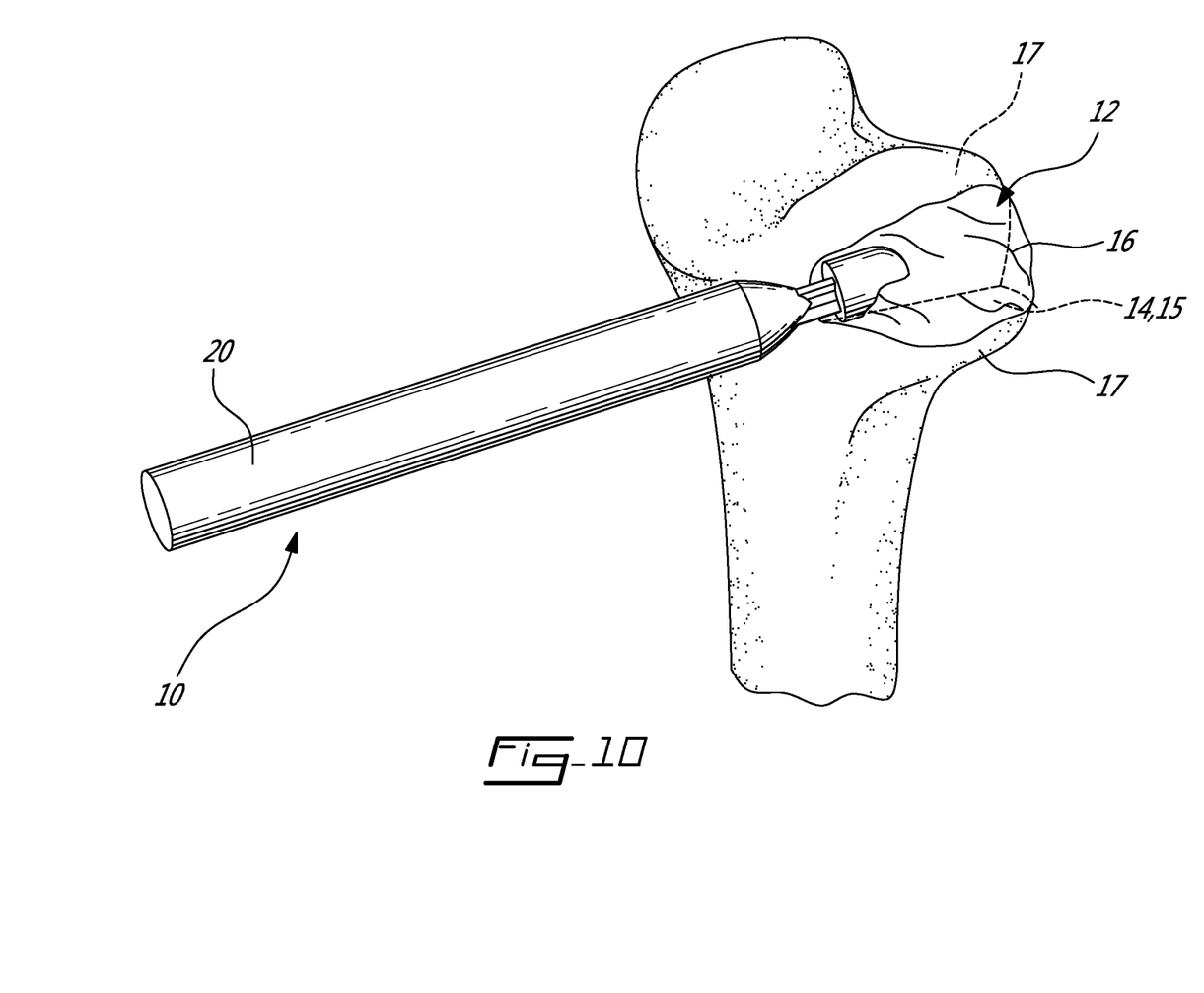
FIG. 10 is a tridimensional schematic view of the tool with the body thereof inserted in a cut section of a bone during the method of FIG. 9.

In another particular embodiment where the digital prosthesis representation is not used and step 66 is omitted, at least part of the virtual border surface portion is defined from the corresponding portion of the virtual bone outer surface 34, and the remainder of the virtual tool outer surface has a generic shape, for example ovoid, planar, or defined as two or more intersecting planar surface sections. An example of such a case is illustrated in FIG. 8. In this embodiment, the part of the virtual border surface portion 354' extending a distance "A" from the lower virtual planar surface 352 along the entire junction of the virtual tool outer surface 354 with this virtual planar surface 352 is defined from the corresponding portion of the virtual bone outer surface 34 extending the distance "A" from the lower virtual cutting plane 32 along the entire junction of the virtual bone outer surface 34 with this virtual cutting plane 32 (FIG. 4). For instance, this part of the virtual border surface portion 354' may be defined by making a copy of the corresponding portion of the virtual bone outer surface 34. In a particular embodiment, the corresponding parts of the virtual border surface portion 354' and the virtual bone outer surface 34 are identical. It is understood that in alternate embodiments, the part of the virtual border surface portion 354' defined from the corresponding portion of the virtual bone outer surface 34 may be defined along only part of the junction with the lower virtual planar surface 352 and/or along part or an entirety of the junction with the other virtual planar surface 352.

When the digital prosthesis representation is used as per step 66, the outer surface of the prosthesis may be defined to mimic the outer surface of the cut section of the bone adjacent one or more cut surface(s). Accordingly, and as shown for example in FIGS. 6A-6B, the virtual tool outer surface 154 may completely correspond to the virtual prosthesis outer surface 144. For instance, the virtual tool outer surface 154 may be defined by making a copy of the virtual prosthesis outer surface 144. In the example shown, the prosthesis is retained in the remaining bone through retaining features extending from one of the contact surfaces of the prosthesis and penetrating into the bone, represented in the digital prosthesis representation 140 (FIG. 6a) by virtual retaining features 146 extending from the lower virtual contact surface 142, with the outer surface of the prosthesis being free of any retaining features. Accordingly, the body 12 of the tool 10 is defined to represents a copy of the visible/exposed portion of the prosthesis when engaged to the remaining bone.

In this embodiment, the part of the virtual prosthesis outer surface 144 extending a distance "A" from the lower virtual contact surface 142 along the entire junction of the virtual prosthesis outer surface 144 with this virtual contact surface 142 (FIG. 6a) is defined from the corresponding portion of the virtual bone outer surface 34 extending the distance "A" from the lower virtual cutting plane 32 along the entire junction of the virtual bone outer surface 34 with this virtual cutting plane 32 (FIG. 4). Accordingly, having the virtual tool outer surface 154 completely corresponding to the virtual prosthesis outer surface 144 results in the part of the virtual border surface portion 154' extending the distance "A" from the lower virtual planar surface 152 along the entire junction of the virtual tool outer surface 154 with this virtual planar surface 152 (FIG. 6b) also being defined from the corresponding portion of the virtual bone outer surface 34 extending the distance "A" from the lower virtual cutting plane 32 along the entire junction of the virtual bone outer surface 34 with this virtual cutting plane 32 (FIG. 4). In a particular embodiment, the corresponding parts of the virtual border surface portion 154' and the virtual bone outer surface 34 are identical. Depending on the configuration of the prosthesis and accordingly of the virtual prosthesis outer surface 144, in alternate embodiments, the part of the virtual border surface portion 154' defined from the corresponding portion of the virtual bone outer surface 34 may be defined along only part of the junction with the lower virtual planar surface 152 and/or along part or an entirety of the junction with the other virtual planar surface 152.

Figure 7B:
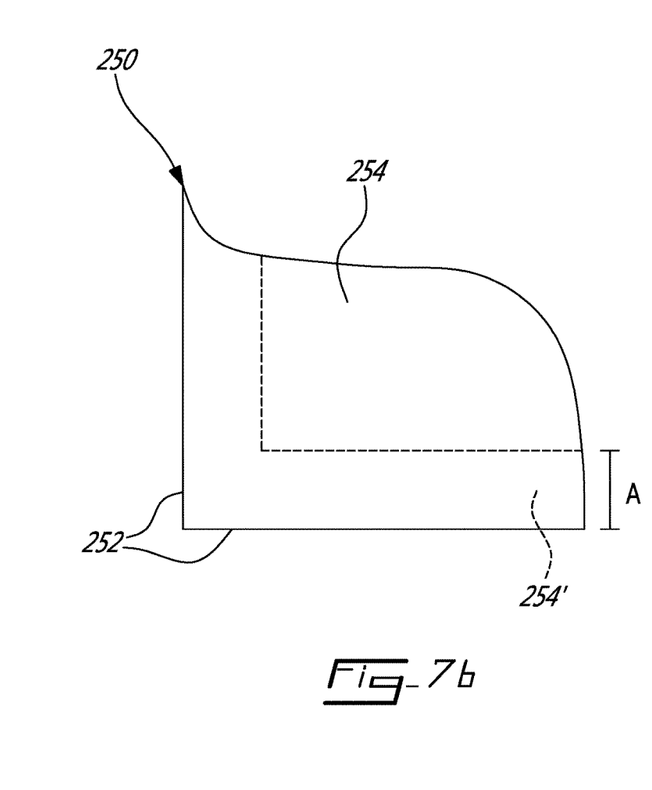

Another embodiment where the digital prosthesis representation is used but where the virtual prosthesis outer surface and the virtual bone outer surface adjacent the cutting planes differ from one another is shown in FIGS. 7a-7b. The prosthesis may include retaining features as part of and/or extending from its outer surface to engage the outer surface of the remaining bone. In the example shown, the prosthesis includes a rim overlapping the outer surface of the bone and other overlapping retaining members, which are represented by virtual retaining features 246 in the digital prosthesis representation 240 of FIG. 7a, with all virtual retaining features 246 being located adjacent the lower virtual planar surface 152. The part of the virtual border surface portion 254' extending the distance "A" from the lower virtual planar surface 252 along the entire junction of the virtual tool outer surface 254 with this virtual planar surface 252 (FIG. 7b) is defined from the corresponding portion of the virtual bone outer surface 34 extending the distance "A" from the lower virtual cutting plane 32 along the entire junction of the virtual bone outer surface 34 with this virtual cutting plane 32 (FIG. 4), and the remainder of the virtual tool outer surface 254 is defined from the corresponding portion B of the virtual prosthesis outer surface 244. For instance, this part of the virtual border surface portion 254' may be defined by making a copy of the corresponding portion of the virtual bone outer surface 34. In a particular embodiment, the corresponding parts of the virtual border surface portion 254' and the virtual bone outer surface 34 are identical. It is understood that in alternate embodiments, the part of the virtual border surface portion 254' defined from the corresponding portion of the virtual bone outer surface 34 may be defined along only part of the junction with the lower virtual planar surface 252 and/or along part or an entirety of the junction with the other virtual planar surface 252. The connection between the two profiles for the virtual tool outer surface 254 is preferably made in a seamless manner. The body 12 of the tool 10 thus represents a copy of the bone near the cut surface(s) and of the visible/exposed portion of the prosthesis elsewhere, such that the body 12 is free of the outer surface retaining features of the prosthesis.

Referring back to FIG. 3, once the digital tool representation 50, 150, 250, 350 is created, the body 12 of the tool 10 is manufactured in step 70. In embodiments where the tool handle 20 is manufactured in one piece with the tool body 12, a digital handle body is added to the digital tool representation 50, 150, 250, 350 before the tool is manufactured. Manufacturing of the body 12 of the tool 10 includes creating each planar surface 14 of the body 12 in correspondence with the respective virtual planar surface 52, 152, 252, 352 of the digital tool representation 50, 150, 250, 350 and creating the outer surface 16 of the body 12 in correspondence with the virtual tool outer surface 54, 154, 254, 354 of the digital tool representation 50, 150, 250, 350. The handle 20 may be manufactured at the same time, or manufactured separately. In a particular embodiment, the body 12 of the tool 10 is manufactured using a rapid prototyping method with the digital tool representation 50, 150, 250, 350 (e.g. CAD model) used directly as input or transformed as required before being input into an appropriate application of a rapid prototyping system, and made from plastic (e.g. polyamide) or metal material. Alternately, the body 12 of the tool 10 (optionally together with the handle 20) may be machined, for example from solid metal, using computer-aided machining (CAM), and machining parameters related for example to the tool material, cutting tools, and cutting operations, may be defined. A machining trajectory used for producing the tool body 12 (optionally together with the handle 20) may then be generated from the digital tool representation 50, 150, 250, 350, and an appropriate computer numerical control (CNC) code specifying the tool paths as well as any additional required information may then be generated and sent to the machining tool over a suitable communication link.

In an embodiment where the planar surface(s) 14 of the body 12 include a textured pattern to be used as a filing tool, the planar surface(s) 14 may be manufactured directly with the textured pattern thereon. Alternately, the textured pattern may be created in a subsequent manufacturing step. In these embodiments, the material used is selected such as to be more resistant than bone such as to be able to use the tool for filing. Examples of suitable materials include, but are not limited to, titanium, stainless steel, and cobalt-chrome.

The tool 10 may be used to validate a cut in a bone in accordance with the method 80 and with reference to the diagram of FIG. 7 and the schematic illustration of FIG. 8. First, at step 82, the body 12 of the tool 10 is inserted into the cut section of the bone, with each outer surface 14 of the body 12 in contact with the respective cut surface 15 of the bone. In a particular embodiment, the handle 20 facilitates manipulation of the body 12 for proper placement thereof into the cut section.

At step 84, the body 12 is moved until the outer surfaces 16, 17 of the body 12 and of the remaining bone are as close to alignment as possible at the junction therebetween. At least part of the border portion 16' of the outer surface 16 of the tool is configured to correspond to the outer surface of the nominal removed bone section adjacent the corresponding junction with the cut surface(s) 15. Accordingly, this part of the border portion 16' defines a reference portion of the outer surface 16 of the tool.

This reference portion and the outer surface of the bone 17 should be continuous or substantially continuous with one another at the junction between the two if the cut section of the bone corresponds to the nominal cut section of the bone. The junction between the reference portion of the outer surface 16 of the tool and the bone outer surface 17 is thus examined at step 86, to determine if the outer surfaces 16, 17 are continuous or substantially continuous along that junction. If the reference portion of the tool 12 protrudes beyond the corresponding outer surface 17 of the bone, the body 12 is removed from the cut and the size of the cut section is increased, as illustrated in step 88, and steps 82 to 86 are repeated until the outer surfaces 16, 17 are continuous or substantially continuous along the junction. In a particular embodiment, the size of the cut section is increased by filing at least one of the cut surfaces 15 with the corresponding planar surface 14 of the body 12 which defines a filing tool through an appropriate textured pattern.

If the corresponding outer surface 17 of the bone protrudes beyond the reference portion of the tool 12, shimming material and/or cement and/or any adequate filler may be required to position the prosthesis. Preferably, the bone is initially cut to obtain a cut section smaller than the nominal cut section, and progressively enlarged while verifying the size of the cut section with the tool 12 between each step, such as to reduce the risks of requiring such additional materials.

In a particular embodiment where the body 12 of the tool 10 represents the custom prosthesis at least away from the cut surface(s) 15, once the reference portion of the tool outer surface 16 and the bone surface 17 are continuous or substantially continuous, the body 12 of the tool 10 is further used to verify a fit between the custom prosthesis and an adjacent bone or prosthesis. At step 90, the articulation is moved throughout its range of motion with the body 12 in place in the cut section, and the fit is verified. In a particular embodiment, such verification includes verifying that a tension in the ligaments of the articulation is adequate. The tool 10 may thus allow confirming of the dynamic interaction of the corresponding prosthesis within the articulation before the prosthesis is installed.

The above description is meant to be exemplary only, and one skilled in the art will recognize that changes may be made to the embodiments described without departing from the scope of the invention disclosed. Modifications which fall within the scope of the present invention will be apparent to those skilled in the art, in light of a review of this disclosure, and such modifications are intended to fall within the appended claims.

The invention claimed is:

1. A surgical cut validation tool for validating a cut in a bone, the cut defining a nominal section to be removed from the bone having at least one nominal cut surface, the cut further defining a remaining bone having at least one cut surface created when the nominal section is removed, the surgical cut validation tool comprising:
    a body having
        at least one planar remaining bone contacting surface, and
        an outer surface extending from the at least one planar remaining bone contacting surface, the outer surface including a border surface portion extending from and adjacent to a junction between the outer surface and each one of the at least one planar remaining bone contacting surface;
        wherein each one of the at least one planar remaining bone contacting surface matches a respective one of the at least one nominal cut surface of the nominal section, and each one of the at least one planar remaining bone contacting surface conforms to a corresponding one of the at least one cut surface of the remaining bone created when the nominal section is removed and is superposable against the corresponding one of the at least one cut surface of the remaining bone in a predetermined configuration; and
        at least part of the border surface portion has a shape matching a shape of a corresponding part of an outer surface of the nominal section, the at least part of the border surface portion having a same relative position with respect to each one of the at least one planar remaining bone contacting surface than the part of the outer surface of the nominal section with respect to a corresponding one of the at least one nominal cut surface of the nominal section, said at least part of the border surface portion being shaped to be substantially aligned with an outer surface of the remaining bone adjacent to a junction of the at least one cut surface of the remaining bone when the body is superposed to the remaining bone in the predetermined configuration; and
        wherein only the at least one planar remaining bone contacting surface contacts the remaining bone.

2. The surgical cut validation tool as defined in claim 1, wherein the shape of an entirety of the border surface portion corresponds to the shape of the corresponding part of the outer surface of the nominal.

3. The surgical cut validation tool as defined in claim 1, wherein an entirety of the outer surface of the body has a shape corresponding to a shape of the outer surface of the nominal section.

4. The surgical cut validation tool as defined in claim 1, wherein the outer surface of the body away from the at least part of the border surface portion is configured to correspond to an outer surface of a custom prosthesis configured for replacing the nominal section.

5. The surgical cut validation tool as defined in claim 4, wherein an entirety of the outer surface of the body corresponds to the outer surface of the custom prosthesis.

6. The surgical cut validation tool as defined in claim 1, wherein the at least one planar remaining bone contacting surface includes two intersecting planar surfaces.

7. The surgical cut validation tool as defined in claim 1, wherein each one of the at least one planar remaining bone contacting surface of the body has a textured surface pattern such that the planar surface can be used as a filing tool.

8. The surgical cut validation tool as defined in claim 1, further comprising a handle detachably connectable to the outer surface of the body.

9. A surgical cut validation tool for validating a cut forming in a bone a nominal section to be removed from the bone and having at least one nominal cut surface, and a remaining bone having at least one cut surface, the at least one cut surface of the remaining bone corresponding to a respective one of the at least one nominal cut surface of the nominal section, the surgical cut validation tool comprising:
    a body having
        at least one planar remaining bone contacting surface, each one of the at least one planar remaining bone contacting surface corresponding to one of said at least one nominal cut surface of the nominal section and being receivable against a corresponding one of said at least one cut surface of the remaining bone, and
        an outer non-bone contacting surface extending from the at least one planar remaining bone contacting surface, the outer non-bone contacting surface including a border surface portion extending from a junction between the outer non-bone contacting surface and each one of the at least one planar remaining bone contacting surface;
        wherein at least part of the border surface portion has a shape duplicating a shape of a corresponding part of an outer non-bone contacting surface of the nominal section, the at least part of the border surface portion having a same relative position with respect to each one of the at least one planar remaining bone contacting surface than the corresponding part of the outer non-bone contacting surface of the nominal section with respect to a corresponding one of said at least one nominal cut surface of the nominal section, said at least part of the border surface portion forming a continuity with an outer non-bone contacting surface of the remaining bone at a junction with a corresponding one of the at least one cut surface of the remaining bone; and wherein
        the at least one planar remaining bone cut contacting surface is comprised of one or more planar surfaces.

10. A surgical cut validation tool for validating a cut in a bone, the cut separating the bone into a nominal section to be removed from the bone and a remaining bone having at least one cut surface created when the nominal section is removed, the surgical cut validation tool comprising:

a body having at least one planar remaining bone contacting surface conforming to the at least one cut surface of the remaining bone created when the nominal section is removed, and an outer non-bone contacting surface extending from the at least one planar remaining bone contacting surface, the body being superposable against the cut surface of the remaining bone when the nominal section is removed in a predetermined configuration with the at least one planar remaining bone contacting surface being juxtaposed against a respective one of said at least one cut surface of the remaining bone with a junction between the outer non-bone contacting surface and the at least one planar remaining bone contacting surface being in register with a perimeter of the remaining bone delimitating the at least one cut surface along at least a portion thereof and the outer non-bone contacting surface forms a continuous projection of the remaining bone at the junction between the outer non-bone contacting surface and the at least one planar remaining bone contacting surface.

11. The surgical cut validation tool of claim 10, wherein the body is delimited by the at least one planar remaining bone contacting surface and the outer non-bone contacting surface.

12. The surgical cut validation tool of claim 10, wherein the junction between the outer non-bone contacting surface and the at least one planar remaining bone contacting surface is in register with the perimeter of the remaining bone delimitating the at least one cut surface along its entire length.

13. The surgical cut validation tool as defined in claim 10, wherein an entirety of the outer non-bone contacting surface of the body has a shape corresponding to a shape of an outer surface of the nominal section.

14. The surgical cut validation tool as defined in claim 10, wherein the outer non-bone contacting surface of the body is configured to correspond at least partially to an outer surface of a custom prosthesis configured for replacing the nominal section.

15. The surgical cut validation tool as defined in claim 14, wherein an entirety of the outer non-bone contacting surface of the body corresponds to the outer surface of the custom prosthesis.

16. The surgical cut validation tool as defined in claim 10, wherein the at least one planar remaining bone contacting surface includes two intersecting planar bone contacting surfaces.

17. The surgical cut validation tool as defined in claim 10, wherein each one of the at least one planar remaining bone contacting surface of the body has a textured surface pattern such that the planar bone contacting surface can be used as a filing tool.

18. The surgical cut validation tool as defined in claim 10, further comprising a handle detachably connected to the body.

19. The surgical cut validation tool as defined in claim 1, wherein the at least one nominal cut surface of the nominal section and the at least one cut surface of the remaining bone are predetermined.

20. The surgical cut validation tool as defined in claim 10, wherein the at least one cut surface of the remaining bone is predetermined.

21. The surgical cut validation tool as defined in claim 9, wherein only the at least one planar remaining bone contacting surface is superposed to the remaining bone.

22. The surgical cut validation tool as defined in claim 10, wherein only the at least one planar remaining bone contacting surface is superposed to the remaining bone.

23. The surgical cut validation tool as defined in claim 1, wherein the body further comprises a mortise defined in the outer surface and being configured to receive a handle tenon therein.

24. The surgical cut validation tool as defined in claim 9, wherein the body further comprises a mortise defined in the outer surface and being configured to receive a handle tenon therein.

25. The surgical cut validation tool as defined in claim 10, wherein the body further comprises a mortise defined in the outer surface and being configured to receive a handle tenon therein.

\* \* \* \* \*